United States Patent [19]

Plath et al.

[11] Patent Number: 4,566,900

[45] Date of Patent: Jan. 28, 1986

[54] ANILINE DERIVATIVES AND THEIR USE FOR CONTROLLING UNDESIRABLE PLANT GROWTH

[75] Inventors: Peter Plath, Ludwigshafen; Ulrich Schirmer, Heidelberg; Gernot Reissenweber, Ludwigshafen; Bruno Wuerzer, Otterstadt; Guenter Retzlaff, Roemerberg, all of Fed. Rep. of Germany

[73] Assignee: BASF Aktiengesellschaft, Fed. Rep. of Germany

[21] Appl. No.: 445,702

[22] Filed: Dec. 1, 1982

[30] Foreign Application Priority Data

Dec. 9, 1981 [DE] Fed. Rep. of Germany ....... 3148594

[51] Int. Cl.$^4$ .................... C07C 155/02; C07C 83/10; A01N 37/00; A01N 37/44
[52] U.S. Cl. ............................. 71/100; 260/453 RW; 260/455 A; 564/221; 564/202; 564/211; 564/189; 564/190; 564/123; 564/452; 564/430; 564/62; 560/27; 560/28; 71/111; 71/118; 71/120; 544/165; 546/226; 548/538

[58] Field of Search .................. 260/453 RW, 455 A; 564/221, 202, 211, 189, 190, 123, 452, 430, 62; 560/27, 28; 71/100, 118, 120, 111

[56] References Cited

FOREIGN PATENT DOCUMENTS 2828417 1/1979 Fed. Rep. of Germany ...... 260/453 RW

Primary Examiner—Henry R. Jiles
Assistant Examiner—Robert C. Whittenbaugh
Attorney, Agent, or Firm—Keil & Weinkauf

[57] ABSTRACT

Aniline derivatives of the formula

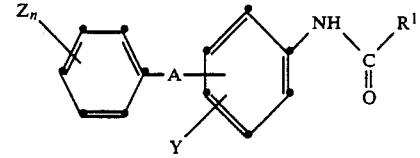

where $R^1$, Y, A, Z and n have the meanings given in the description, are used for controlling undesirable plant growth.

8 Claims, No Drawings

ANILINE DERIVATIVES AND THEIR USE FOR CONTROLLING UNDESIRABLE PLANT GROWTH

The present invention relates to aniline derivatives, herbicides containing these compounds as active ingredients, and a process for controlling undesirable plant growth using these compounds.

It has been disclosed that N-methoxy-N-methyl-N'-phenylureas have herbicidal actions (German Laid-Open Application DOS No. 2,828,417).

We have found that aniline derivatives of the formula

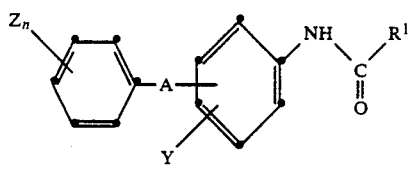

where $R^1$ is alkoxy, alkylthio or unsubstituted, halogen-substituted or $C_1$–$C_4$-alkoxy-substituted alkyl, each of which is of no more than 4 carbon atoms, or is cycloalkyl of 3 to 6 carbon atoms or the radical

where $R^2$ and $R^3$ independently of one another are each hydrogen, alkyl or alkoxy, each of no more than 4 carbon atoms, or cycloalkyl of 3 to 6 carbon atoms, or $R^2$ and $R^3$ together form an alkylene chain of no more than 6 carbon atoms which in unsubstituted or methyl-substituted and may or may not contain oxygen as a chain member, Y is hydrogen, halogen, methyl, methoxy or trifluoromethyl, A is an alkylene chain of 2 to 9 carbon atoms which contains a carbonyl group or a carbinol group of the formula

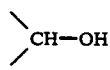

and can be substituted by methyl, Z is hydrogen, halogen, alkyl, alkoxy, haloalkyl or haloalkoxy, each of no more than 6 carbon atoms, or phenyl or phenoxy, and n is 1, 2 or 3, and the radical

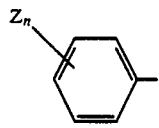

can be replaced by naphthyl which is unsubstituted or substituted by halogen, or by alkyl or alkoxy, each of no more than 4 carbon atoms, have a herbicidal action and are well tolerated by a number of crops.

In formula I, $R^1$ can be alkoxy, alkylthio or unsubstituted, halogen-substituted or $C_1$–$C_4$-alkoxy-substituted alkyl, each of no more than 4carbon atoms, eg. methoxy, ethoxy, n-propoxy, isopropoxy, sec.-butoxy, tert.butoxy, methylthio, ethylthio, n-propylthio, sec.-butylthio, tert.-butylthio, methyl, ethyl, n-propyl, n-butyl, sec.-butyl, tert.-butyl, isobutyl, chloromethyl, 1,1-dichloroethyl, dichloromethyl, methoxymethyl, 1-methoxyethyl or 2-methoxyethyl, cycloalkyl of 3 to 6 carbon atoms, eg. cyclopropyl, cyclopentyl or cyclohexyl, or the radical

where $R^2$ and $R^3$ independently of one another are each hydrogen, or alkyl or alkoxy, each of no more than 4 carbon atoms, eg. methyl, ethyl, isopropyl, n-butyl, sec.-butyl, isobutyl, tert.-butyl, methoxy or ethoxy, or cycloalkyl of 3 to 6 carbon atoms, eg. cyclopropyl, cyclopentyl or cyclohexyl, or $R^2$ and $R^3$ together form an alkylene chain of no more than 6 carbon atoms which is unsubstituted or substituted by methyl and may or may not contain oxygen as a chain member, eg. trimethylene, tetramethylene, 1,4-dimethyltetramethylene, pentamethylene, hexamethylene, 3-oxapentamethylene, 1-oxa-pentamethylene or 1-oxatetramethylene, Y can be hydrogen, halogen, eg. fluorine, chlorine or bromine, methyl, methoxy or trifluoromethyl, A can be meta or para to the —NH—CO—$R^1$ group, and can be an alkylene chain of 2 to 9 carbon atoms which contains a carbonyl group or a carbinol group of the formula

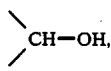

and may be substituted by methyl, eg. a $C_2$-chain, such as —CO—$CH_2$— or —$CH_2$—CO—, or the carbinols, —CH(OH)—$CH_2$— or —$CH_2$—CH(OH)—, obtainable therefrom by reduction, or a $C_3$ chain, such as —CO—$(CH_2)_2$—, —$(CH_2)_2$—CO—, —CO—CH(CH$_3$)—$CH_2$— and —$CH_2$—CH(CH$_3$)—CO—, a $C_4$ chain such as —CO—$(CH_2)_3$—, $(CH_2)_3$—CO—, —$CH_2$—CO—$(CH_2)_2$— and —$(CH_2)_2$—CO—$(CH_2)$—, a $C_5$ chain, such as —CO—$(CH_2)_4$—, —$(CH_2)_4$—CO—, —$(CH_2)_2$—CO—$(CH_2)_2$—, —CO—$(CH_2)_2$—CH(CH$_3$)—$CH_2$— and —$CH_2$—CH(CH$_3$)—$(CH_2)_2$—CO—, a $C_6$ chain, such as —CO—$(CH_2)_5$—, —$(CH_2)_5$—CO—, —$CH_2$—CO—$(CH_2)_4$—, —$(CH_2)_4$—CO—$CH_2$—, —$CH_2$—CO—$(CH_2)_2$—CH(CH$_3$)—$CH_2$— and —$CH_2$—CH(CH$_3$)—$(CH_2)_2$—CO—$CH_2$— a $C_7$ chain, such as —CO—$(CH_2)_6$—, —$(CH_2)_6$—CO—$(CH_2$-$)_3$—CO—$(CH_2)_3$—, —$(CH_2)_2$—CO—$(CH_2)_4$—, —$(CH_2)_4$—CO—$(CH_2)_2$—$CH_2$—CH(CH$_3$)—$(CH_2$-$)_2$—CO—$(CH_2)_2$— and —$(CH_2)_2$—CO—$(CH_2$-$)_2$—CH(CH$_3$)—$CH_2$, a $C_8$ chain, such as —CO—$(CH_2$-$)_7$— and —$(CH_2)_7$—CO—, or a $C_9$ chain, such as —CO(CH$_2$)$_8$—, —$(CH_2)_8$—CO—, —$(CH_2$-$)_4$—CO—$(CH_2)_4$—, —$CH_2$—CH(CH$_3$)—$(CH_2$-$)_2$—CO—$(CH_2)_4$— and —$(CH_2)_4$—CO—$(CH_2$-$)_2$—CH(CH$_3$)—$CH_2$—, or the carbinols obtainable from any of the above alkylene chains, Z is ortho, meta or para to A, and can be hydrogen, halogen, eg. fluorine chloride or bromine, alkyl, alkoxy, haloalkyl or haloalkoxy, each of no more than 6 carbon atoms, eg. methyl, ethyl, isopropyl, tert.-butyl, n-hexyl, methoxy, ethoxy, isopropoxy, tert.-butoxy, n-hexoxy, trifluoromethyl, 1,1,2-trifluoro-2-chloroethoxy, difluoromethoxy, phenyl or phenoxy, and n is preferably 1, but can furthermore be 2 or 3, in particular where Z is fluorine, chlorine, bromine or methyl.

In formula I, the radical

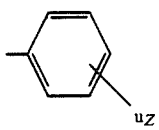

may furthermore be replaced by an α- or β-naphthyl radical which may be substituted by halogen, eg. chlorine or bromine, or by alkyl or alkoxy, each of no more than 4 carbon atoms, eg. methyl, ethyl, methoxy, ethoxy, isopropyl or tert.-butoxy.

Preferred compounds of the formula I are those in which $R^1$ is

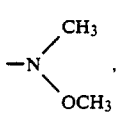

Y is hydrogen or halogen, in particular chlorine, A is —CO—$(CH_2)_2$— in the para-position to —NH—CO—$R^1$, Z is halogen, in particular chlorine, or alkyl of no more than 4 carbon atoms, in particular methyl, and n is 1.

The aniline derivatives of the formula I are obtained by a process wherein an amine of the formula

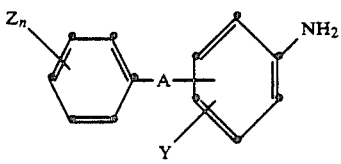

where A, Y, Z and n have the above meanings, is reacted with a compound of the formula $R^1$—CO—X         (III)

where $R^1$ has the above meanings and X is a leaving group, preferably halogen, eg. chlorine or bromine, or $R^1$—CO—O—.

The reaction is carried out in an inert organic solvent, suitable examples being ethers, such as tetrahydrofuran, dimethoxyethane, diethyl ether or methyl tert.-butyl ether, esters, such as ethyl acetate, aliphatic or aromatic hydrocarbons and aliphatic or aromatic chlorohydrocarbons, such as toluene or dichloromethane, and pyridine. Mixtures of these solvents may also be used. The solvent is used in an amount of from 100 to 5,000% by weight, based on the amine of the formula II.

Advantageously, the reaction is carried out in the presence of an acid acceptor, suitable examples being alkali metal hydroxides, alkali metal carbonates, alkali metal bicarbonates, alkaline earth metal hydroxides, alkaline earth metal carbonates, alkaline earth metal bicarbonates, alkaline earth metal oxides or amines, eg. sodium bicarbonate, potassium carbonate, triethylamine, pyridine, N,N-dimethylaniline, N,N-dimethyl-N-cyclohexylamine or quinoline. From 1 to 4 moles of the acid acceptor are employed per mole of the compound of the formula III.

The starting materials of the formulae II and III are preferably employed in equimolar amounts for the reaction, which is carried out at from 20° to 80° C., preferably from 20° to 30° C.

The amines of the formula II are new, and can be obtained by conventional processes, by aldol condensation followed by hydrogenation of the product. For example, an unsubstituted or substituted acetophenone is reacted with a nitrobenzaldehyde to give a nitrochalcone:

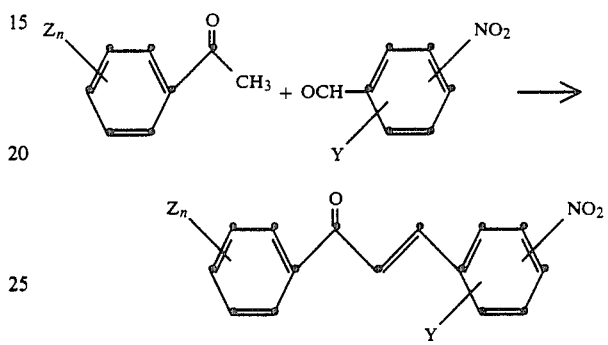

and the nitrochalcone obtained is hydrogenated in a conventional manner in an organic solvent, eg. methanol, tetrahydrofuran, acetic acid or methyl acetate, in the presence of palladium on charcoal or of Raney nickel at from 20° to 150° C., preferably from 20° to 80° C., under atmospheric or superatmospheric pressure. In these formulae, Y, Z and n have the above meanings.

Amines of the formula II, in which A is —CO—$(CH_2)_4$— or —CO—$(CH_2)_2$—CH($CH_3$)—$CH_2$—, are obtained by a process wherein an unsubstituted or substituted acetophenone is condensed with a nitrocinnamaldehyde, for example in accordance with the following equation:

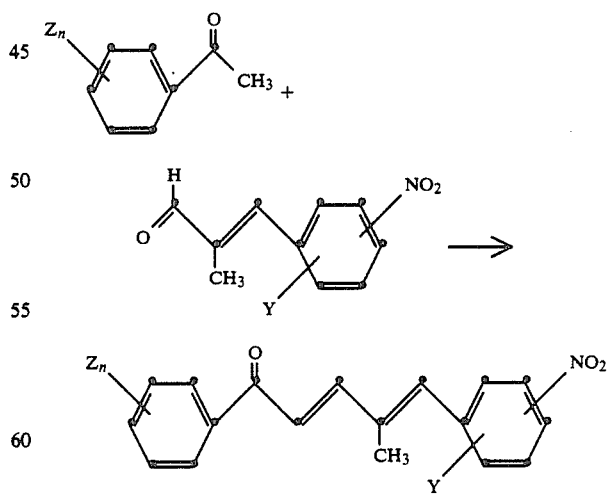

Another possible method of synthesizing amines of the formula II comprises condensing an unsubstituted or substituted benzaldehyde or cinnamaldehyde with a nitroacetophenone, in accordance with the following equation:

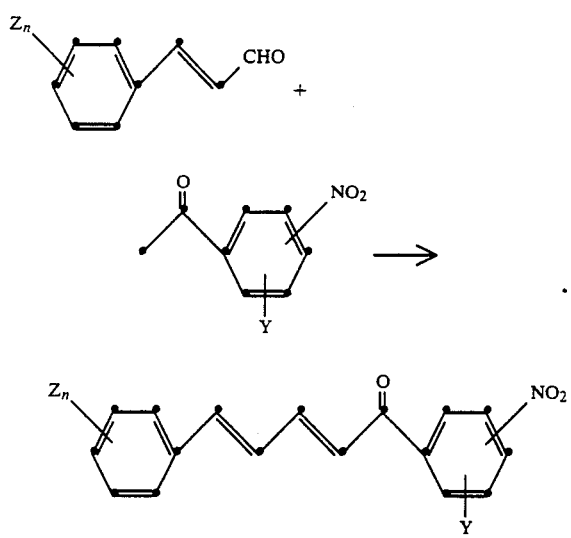

It may also be advantageous to use unsubstituted or substituted benzalacetone as a starting compound, and to condense it with a nitrobenzaldehyde or a nitrocinnamaldehyde:

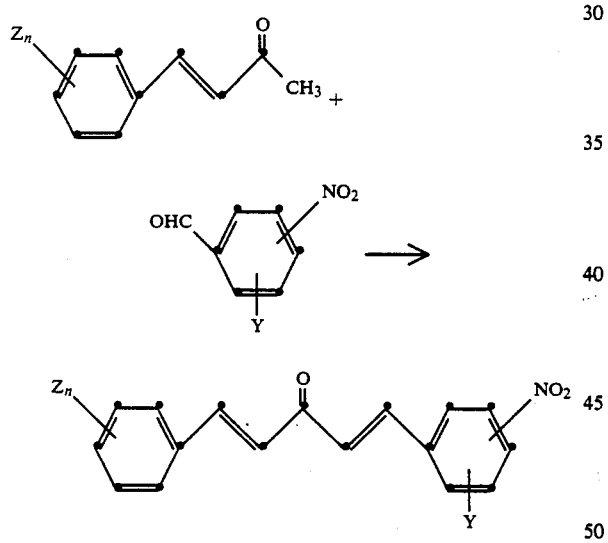

In all three variants, the product is catalytically hydrogenated.

Amines of the formula II, in which A is —(CH$_2$)$_p$—CO— where p is an integer from 1 to 8, can be obtained by Friedel-Crafts acylation of a carboxylic acid chloride of the formula

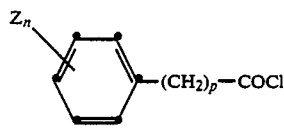 (V)

where Z, n and p have the above meanings, in accordance with the equation

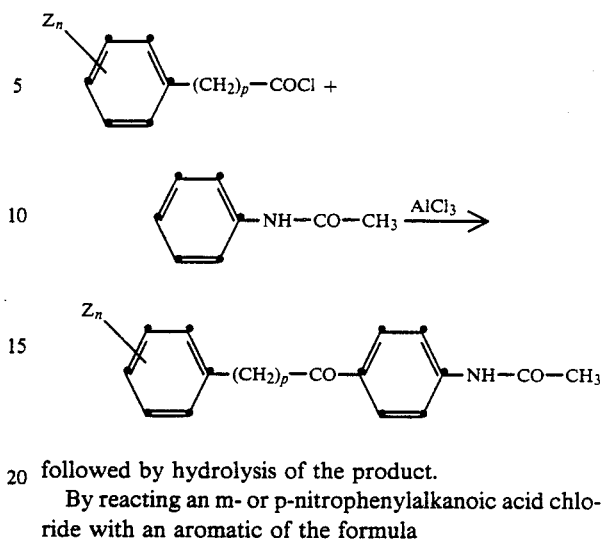

followed by hydrolysis of the product.

By reacting an m- or p-nitrophenylalkanoic acid chloride with an aromatic of the formula

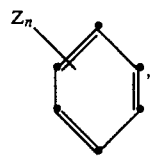

where Z and n have the above meanings, the following nitrophenyl alkylaryl ketones are obtained:

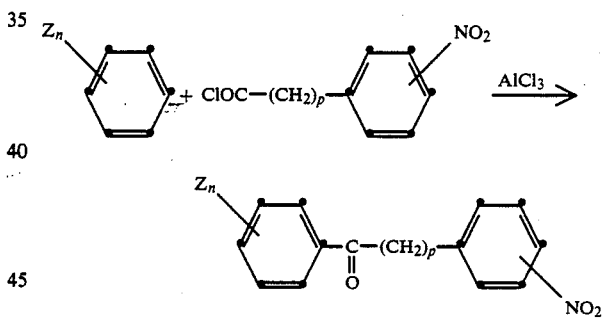

It is also possible to subject an ω-phenylalkanoic acid chloride to a Friedel-Crafts reaction with

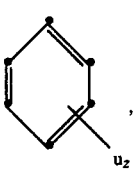

and subsequently to nitrate the resulting ω,α-diarylakyl ketones in the para-position to —(CH$_2$)$_p$—:

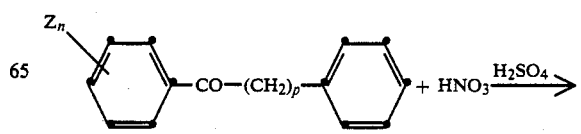

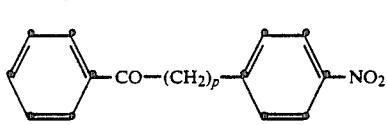

The nitrophenylketones thus obtained can be catalytically hydrogenated to give anilines of the formula VI:

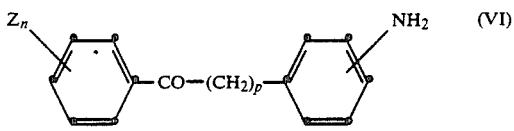

In these formulae, p is an integer from 1 to 8. (G. Olah, Friedel-Crafts and Related Reactions, Vol. III, Part I, pages 23, 24, 1,393 et seq., Interscience Publishers, New York, 1964).

The absorption of hydrogen during the hydrogenation of the above saturated or unsaturated nitrophenylketones is a stepwise procedure, which can be either terminated at the stage of the saturated anilinoketone or continued until the anilinocarbinol is obtained.

The hydrogenation is carried out in a conventional manner in the presence of Raney nickel or, preferably, palladium on active charcoal. In this case, hydrogenation to give the saturated anilinoketone is carried out at as low as 0°–30° C., preferably 25° C., and under a pressure of 1.01–20 bar, preferably 1.1 bar. Prolonging the reaction time, increasing the hydrogenation temperature and/or increasing the pressure to 50 bar result in reduction of the keto group to the carbinol group. The keto group is more readily hydrogenated the closer it is to one of the two benzene rings (Houben-Weyl Methoden der Org. Chemie, Vol. 4/1c, pages 13 et seq., Georg Thieme Verlag, Stuttgart, 1980).

The Examples which follow illustrate the synthesis of the amines of the formula II:

EXAMPLE A 1-(4-Methylphenyl)-3-(4-aminophenyl)-n-propan-1-one

In a 2 liter stirred apparatus with a water-separating head, a mixture of 272 g of 4-nitrobenzaldehyde, 255 g of 4-methylacetophenone, 40 g of boron trioxide and 400 ml of xylene was heated at the boil for 8 hours, after which 32 ml of water had separated off. The reaction solution was allowed to cool and then poured into 1 liter of toluene, the precipitated solid was filtered off under suction, and dried under reduced pressure, and 391 g (81% of theory) of a yellow solid of melting point 163°–165° C. were obtained. 189 g of this nitro compound were dissolved in 2 liters of tetrahydrofuran, and 5 g of 10% strength Pd on animal charcoal (Degussa type E 10N) were added to the solution. The apparatus was flushed with nitrogen, after which hydrogenation was carried out at 20° C. under slightly superatmospheric pressure (1.1 bar) until 64.5 liters of hydrogen had been absorbed. Thereafter, the supply of hydrogen was interrupted, the catalyst was filtered off and the solvent was stripped off under reduced pressure. The residue was stirred with diisopropyl ether, and the product was filtered off under suction. 159 g (94% of theory) of a yellowish crystalline solid of melting point 59°–61° C. were obtained.

EXAMPLE B 1-(4-Methylphenyl)-5-(4-aminophenyl)-n-pentan-3-one 15 g of a 10% strength NaOH solution was added dropwise, while cooling with ice, to a mixture of 80 g of 1-(4-methylphenyl)-but-2-en-3-one, 83 g of 4-nitrobenzaldehyde and 600 ml of ethanol at 25° C. After the addition was complete, the mixture was stirred for a further hour at 25° C. Thereafter, the product was filtered off under suction and the solid obtained was recrystallized from ethyl acetate. 135 g (92% of theory) of 1-(4-methylphenyl)-5-(4'-nitrophenyl)-1,4-pentadien-3-one of melting point 182°–184° C. were obtained.

60 g of the pentadienone thus obtained were dissolved in 2 liters of tetrahydrofuran, and 6 g of 10% strength Pd on animal charcoal (Degussa type E 10N) were added to the solution. The hydrogenation apparatus was then flushed with nitrogen, after which hydrogenation was carried out at from 22° to 26° C. under 1.1 bar for 2½ hours, 24 liters of hydrogen being absorbed. The catalyst was filtered off, and the filtrate was dried over MgSO4 and then evaporated to give 49 g (89.5% of theory) of an oil whose IR spectrum indicated the presence of the —NH2— group and the CO group, and which has the following structure:

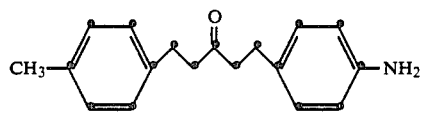

EXAMPLE C 1-(4-Aminophenyl)-7-phenyl-n-heptan-3-one 16.2 g of a 10% strength NaOH solution were added dropwise, while cooling slightly, to a mixture of 46.5 g of cinnamalacetone, 45.4 g of p-nitrobenzaldehyde and 160 ml of ethanol at 25° C. The reaction mixture became clear after a short time, and a yellow solid subsequently separated out. The mixture was stirred for one hour, after which the solid was filtered off under suction, washed with diethyl ether, and dried under reduced pressure to give 76 g (91% of theory) of 1-(4-nitrophenyl)-7-phenyl-1,4,6-heptatrien-3-one of melting point 168°–170° C.

35 g of this product were hydrogenated in the presence of 3.5 g of 10% strength Pd on animal charcoal, in 350 ml of tetrahydrofuran, under 1.1 bar, until 15 liters of hydrogen had been absorbed. The catalyst was filtered off, the filtrate was dried over MgSO4 and the solvent was stripped off to give 26 g (80.5% of theory) of an oil whose IR spectrum indicated the presence of the NH2 group and the CO group, and which has the following structure:

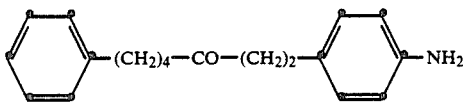

EXAMPLE D

1-(4-Aminophenyl)-3-methyl-5-(4-methylphenyl)-n-pentan-5-one 25 ml of a 5% strength NaOH solution were added dropwise to a mixture of 95.5 g of 4-nitro-α-methylcinnamaldehyde, 74 g of 4-methylacetophenone and 500 ml of ethanol at 25°-30° C. As a result of the exothermic reaction, the mixture warmed up to 35° C. It was stirred for 2 hours at 35°-40° C. and then allowed to cool, the precipitated solid was filtered off under suction, washed with cold methanol and dried under reduced pressure, and 124 g (83% of theory) of 1-(4-nitrophenyl)-3-methyl-5-(4'-methylphenyl)-2,4-pentadien-5-one of melting point 149°-151° C. were obtained.

Catalytic hydrogenation with a 10% strength Pd/animal charcoal catalyst was carried out in tetrahydrofuran, using a procedure similar to that described in Example C. The hydrogenation produced two substances, which were separated by chromatography over silica gel, using a 1:1 ethyl acetate/cyclohexane mixture as the eluant. 7 g of 1-(4-aminophenyl)-3-methyl-5-(4-methylphenyl)-n-pentan-5-one were obtained from 20 g of the hydrogenation product. The second substance was the corresponding carbinol of the empirical formula $C_{19}H_{25}NO$.

EXAMPLE E

1-(4-Methylphenyl)-3-(4-aminophenyl)-n-propan-1-ol 60 g of the 1-(4-methylphenyl)-3-(4-aminophenyl)-n-propan-1-one prepared as described in Example A were hydrogenated, in 1 liter of tetrahydrofuran, in the presence of 5 g of 10% strength Pd on charcoal, under 1.1 bar, until 5.5 liters of hydrogen had been absorbed. The catalyst was separated off and the reaction solution was evaporated down, and the oil obtained crystallized on trituration with diisopropyl ether. After the white crystals had been dried, 53 g (88% of theory) of the carbinol of melting point 63°-65° C. were obtained.

EXAMPLE F

1-(3-Aminophenyl)-5-phenyl-n-pentan-1-ol

Using a procedure similar to that described in Example D, 33 g of 3-nitroacetophenone and 26.2 g of cinnamaldehyde in 200 ml of ethanol were condensed in the presence of 10 ml of a 5% strength NaOH solution to give 38 g (71% of theory) of 1-(3-nitrophenyl)-5-phenyl-2,4-pentadien-1-one of melting point 127°-129° C.

Using a procedure similar to that described in Example E, this ketone was hydrogenated until absorption of $H_2$ was complete, and the reaction mixture was worked up to give 28.5 g (79% of theory) of a white crystalline solid of melting point 58°-60° C.

The following amines of the formula II were synthesized in a similar manner:

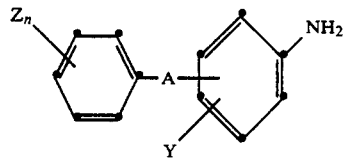

| Position of A | A | Y | $Z_n$ | Mp. [°C.] |
|---|---|---|---|---|
| 3 | —(CH$_2$)$_2$—CO— | H | H | 85-87 |
| 3 | —CO—(CH$_2$)$_2$— | H | 4-Cl | 66-69 |
| 3 | —(CH$_2$)$_2$—CO— | H | 4-CH$_3$ | |
| 3 | —(CH$_2$)$_2$—CO— | H | 4-Cl | |
| 3 | —(CH$_2$)$_2$—CO— | H | 3-CF$_3$ | 134-136 |
| 3 | —(CH$_2$)$_2$—CO— | H | 3,4-Cl$_2$ | 97-100 |
| 3 | —CO—(CH$_2$)$_2$— | 4-Br | H | |
| 3 | —CO—(CH$_2$)$_2$— | H | 2-CH$_3$ | |
| 3 | —CO—(CH$_2$)$_2$— | H | 3-CH$_3$ | |
| 4 | —CO—(CH$_2$)$_2$— | H | H | |
| 4 | —CO—(CH$_2$)$_2$— | H | 4-Cl | |
| 4 | —CO—(CH$_2$)$_2$— | H | 2,4,6-(CH$_3$)$_3$ | oil; Bp. = 187° C./0.3 |
| 4 | —CO—(CH$_2$)$_2$— | 3-Cl | 4-CH$_3$ | |
| 4 | —CO—(CH$_2$)$_2$— | 3-CH$_3$ | 4-CH$_3$ | |
| 4 | —CO—(CH$_2$)$_2$— | 3-OCH$_3$ | 4-CH$_3$ | |
| 4 | —CO—(CH$_2$)$_2$— | 3-CF$_3$ | 4-CH$_3$ | |
| 4 | —CO—(CH$_2$)$_2$— | H | 3-Cl | |
| 4 | —CO—(CH$_2$)$_2$— | H | 4-CF$_3$ | |
| 4 | —CO—(CH$_2$)$_2$— | H | 4-C$_6$H$_5$ | |
| 4 | —(CH$_2$)$_2$—CO— | H | H | |
| 4 | —(CH$_2$)$_2$—CO— | H | 4-CH$_3$ | 113-115 |
| 4 | —(CH$_2$)$_2$—CO— | H | 4-Cl | 103-106 |
| 4 | —(CH$_2$)$_2$—CO— | H | 3-OC$_6$H$_5$ | |
| 4 | —(CH$_2$)$_2$—CO— | H | 4-O—n-C$_6$H$_{13}$ | |
| 4 | —CO—CH(CH$_3$)—CH$_2$— | H | 4-CH$_3$ | oil, Bp. = 180-187° C./0.3 |
| 4 | —CO—CH(CH$_3$)—CH$_2$— | H | 4-Cl | oil |
| 4 | —CO—(CH$_2$)$_2$—CH(CH$_3$)—CH$_2$— | H | H | oil |
| 3 | —CO—(CH$_2$)$_2$—CH(CH$_3$)—CH$_2$— | H | 4-CH$_3$ | oil |
| 3 | —(CH$_2$)$_2$—CO—(CH$_2$)$_2$— | H | H | oil |
| 3 | —(CH$_2$)$_2$—CO—(CH$_2$)$_2$— | H | 4-CH$_3$ | oil |
| 4 | —(CH$_2$)$_4$—CO—(CH$_2$)$_2$— | H | 4-CH$_3$ | oil |
| 3 | —CH$_2$—CO— | H | 4-CH$_3$ | |
| 3 | —CO—CH$_2$— | H | 4-CH$_3$ | |
| 4 | —CH$_2$—CO— | H | " | |
| 4 | —CO—CH$_2$— | H | " | |
| 4 | —CO—(CH$_2$)$_3$— | H | " | |
| 4 | —CO—CH$_2$—CH(CH$_3$)— | H | " | |
| 3 | —CH(CH$_3$)—CH$_2$—CO— | H | " | |
| 4 | —C(CH$_3$)$_2$—CH$_2$—CO— | H | " | |

-continued

| Position of A | A | Y | $Z_n$ | Mp. [°C.] |
|---|---|---|---|---|
| 3 | —C(CH$_3$)$_2$—CH$_2$—CO— | H | " | |
| 4 | —CO—(CH$_2$)$_4$— | H | " | |
| 4 | —CO—(CH$_2$)$_5$— | H | " | |
| 4 | —CO—(CH$_2$)$_6$— | H | " | |
| 4 | —CO—(CH$_2$)$_7$— | H | " | |
| 4 | —CO—(CH$_2$)$_8$— | H | " | |
| 3 | —CH(OH)—(CH$_2$)$_2$— | H | H | oil |
| 3 | —CH(OH)—(CH$_2$)$_2$— | H | 4-F | oil |
| 3 | —CH(OH)—(CH$_2$)$_2$— | H | 4-CH$_3$ | |
| 4 | —CH(OH)—(CH$_2$)$_2$— | H | 4-CH$_3$ | 63–65 |
| 4 | —CH(OH)—(CH$_2$)$_2$— | H | 4-Cl | |
| 4 | —CH(OH)—(CH$_2$)$_2$— | H | 4-CF$_3$ | |
| 4 | —CH(OH)—(CH$_2$)$_3$— | H | 4-CH$_3$ | |
| 4 | —CH(OH)—CH(CH$_3$)—CH$_2$— | H | 4-Cl | oil, Bp. = 210–220° C./0.3 |
| 4 | —(CH$_2$)$_2$—CH(OH)—(CH$_2$)$_2$— | H | H | oil |
| 3 | —(CH$_2$)$_2$—CH(OH)—(CH$_2$)$_2$— | H | 4-CH$_3$ | oil |
| 4 | —CH(OH)—CH$_2$—CH(CH$_3$)— | H | " | |
| 3 | —CH(CH$_3$)—CH$_2$—CH(OH)— | H | " | |
| 4 | —C(CH$_3$)$_2$—CH$_2$—CH(OH)— | H | " | |
| 3 | —C(CH$_3$)$_2$—CH$_2$—CH(OH)— | H | " | |
| 4 | —CH(OH)—(CH$_2$)$_4$— | H | " | |
| 4 | —CH(OH)—(CH$_2$)$_5$— | H | " | |
| 4 | —CH(OH)—(CH$_2$)$_6$— | H | " | |
| 4 | —CH(OH)—(CH$_2$)$_7$— | H | " | |
| 4 | —CH(OH)—(CH$_2$)$_8$— | H | " | |
| 3 | —(CH$_2$)$_2$—CH(OH)— | H | 3-CF$_3$ | oil, Bp. = 240° C./0.3 |
| 3 | —(CH$_2$)$_2$—CO— | H | 3-Cl | oil |
| 4 | —CO—(CH$_2$)$_2$— | H | 4-F | oil |
| 3 | —CO—(CH$_2$)$_2$— | H | 4-OCH$_3$ | 98–100 |
| 3 | —CO—(CH$_2$)$_2$— | H | 4-F | 64–66 |

Aniline derivatives of the formula I, in which $R^1$ is alkoxy, alkylthio or

| Position of A | A | Y | 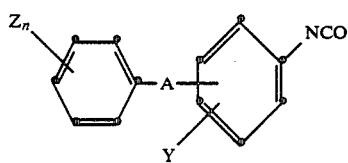 | Mp. [°C.] |
|---|---|---|---|---|
| 3 | —CO—(CH$_2$)$_2$— | H | α-Naphthyl | |
| 3 | —CO—(CH$_2$)$_2$— | H | β-Naphthyl | |
| 4 | —CO—(CH$_2$)$_2$— | H | α-Naphthyl | |
| 4 | —CO—(CH$_2$)$_2$— | H | β-Naphthyl | |

A is a carbonyl-containing alkylene chain of 2 to 9 carbon atoms which can be substituted by methyl, and Y, Z and n have the above meanings, are also obtained by reacting an isocyanate of the formula (IV)

where Y, A, Z and n have the above meanings, with a compound of the formula $R^1H$, where $R^1$ has the above meanings, at from 0° to 150° C., preferably from 10° to 50° C.

The reaction is carried out in a solvent which is inert under the reaction conditions. Suitable solvents are ethers, eg. diethyl ether, methyl tert.-butyl ether or tetrahydrofuran, esters, eg. ethyl acetate, aliphatic or aromatic hydrocarbons and aliphatic or aromatic chlorohydrocarbons, eg. naphtha, toluene, cyclohexane, gasoline, dichloromethane, chloroform, chlorobenzene, o-, m- and p-dichlorobenzene or nitrobenzene, ketones, eg. acetone, nitriles, eg. acetonitrile, and dimethylformamide, as well as mixtures of these.

The reaction of the isocyanates of the formula IV with alcohols, mercaptans or amines of the formula $R^1H$ can, if required, be accelerated by the addition of a catalyst conventionally used for isocyanate reactions, for example tertiary amines, such as triethylamine or 1,4-diazabicyclo[2,2,2]octane, nitrogen heterocyclic compounds, such as pyridine or 1,2-dimethylimidazole, or organic tin compounds, such as dibutyl-tin diacetate or dimethyl-tin dichloride.

The isocyanates of the formula IV are prepared by reacting an amine of the formula III with phosgene (Liebigs Ann. Chem. 562 (1949), 75 et seq.).

The Examples which follow illustrate the preparation of the aniline derivatives of the formula I.

EXAMPLE 1

N-[4-(3-(4-Methylphenyl)-n-propan-3-onyl)-phenyl]-N'-methyl-N'-methoxyurea 15.3 g of sodium bicarbonate were added to a solution, in 250 ml of tetrahydrofuran, of 36 g of the 1-(4-methylphenyl)-3-(4-aminophenyl)-n-propan-1-one prepared as described in Example A, and 18.5 g of N-methyl-N-methoxycarbamyl chloride were added dropwise at 10°–15° C., while cooling with ice. The mixture was stirred for 6 hours at 25° C., after which it was filtered and the filtrate was evaporated down under reduced pressure. The oil obtained crystallized after trituration with diisopropyl ether, and 38.5 g (79% of theory) of product of melting point 73°–74° C. were obtained.

EXAMPLE 2

N-[4-(3-Phenyl-2-methyl-n-propan-3-onyl)-phenyl]-N'-methylurea

A solution of 13.25 g of 4-(3-phenyl-2-methyl-n-propan-3-onyl)-phenyl isocyanate in 20 ml of toluene was added dropwise to a solution of 3 g of methylamine in 100 ml of toluene, at from 20° to 25° C. The mixture was stirred for 6 hours at 40° C., after which the toluene was stripped off under reduced pressure. 13.3 g (90% of theory) of a slightly yellow oil were obtained.

For example, the following compounds of the formula I were or may be synthesized in a similar manner:

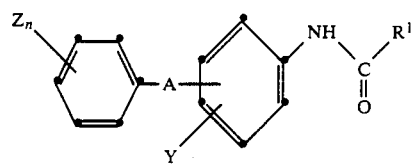

| No. | $R^1$ | Position of A | A | $Z_n$ | Y | M.p. [°C.] |
|---|---|---|---|---|---|---|
| 1 | $-N(CH_3)(OCH_3)$ | 3 | $-(CH_2)_2-(CO)-$ | H | H | 91–92 |
| 2 | " | 3 | $-CO-(CH_2)_2-$ | H | H | 80–82 |
| 3 | " | 3 | $-CO-(CH_2)_2-$ | 4-Cl | H | 102–103 |
| 4 | " | 4 | $-CO-(CH_2)_2-$ | H | H | |
| 5 | " | 4 | $-CO-(CH_2)_2-$ | 4-$CH_3$ | H | 73–74 |
| 6 | " | 4 | $-CO-(CH_2)_2-$ | 4-Cl | H | 107–109 |
| 7 | " | 4 | $-CO-(CH_2)_2-$ | 2,4,6-$(CH_3)_3$ | H | 80–82 |
| 8 | " | 4 | $-CO-CH(CH_3)-CH_2-$ | H | H | 79–81 |
| 9 | $NHCH_3$ | 4 | $-CO-CH(CH_3)-CH_2-$ | H | H | oil |
| 10 | $N(CH_3)_2$ | 4 | $-CO-CH(CH_3)-CH_2-$ | H | H | |
| 11 | $-N(CH_3)(OCH_3)$ | 4 | $-CO-CH(CH_3)-CH_2-$ | 4-Cl | H | oil |
| 12 | " | 4 | $-CO-(CH_2)_2-CH(CH_3)-CH_2-$ | 4-$CH_3$ | H | 86–88 |
| 13 | " | 3 | $-CO-(CH_2)_2-CH(CH_3)-CH_2-$ | 4-$CH_3$ | H | 76–78 |
| 14 | " | 4 | $-(CH_2)_2-CO-$ | 4-Cl | H | 124–126 |
| 15 | " | 4 | $-(CH_2)_2-CO-$ | 4-$CH_3$ | H | 100–102 |
| 16 | " | 3 | $-CO-(CH_2)_2-$ | 4-$OCH_3$ | H | oil |
| 17 | " | 3 | $-CO-(CH_2)_2-$ | 4-F | H | oil |
| 18 | " | 3 | $-(CH_2)_2-CO-$ | 3-$CF_3$ | H | |
| 19 | " | 3 | $-(CH_2)_2-CO-$ | 3,4-$Cl_2$ | H | 112–114 |
| 20 | $C_2H_5$ | 3 | $-(CH_2)_2-CO-(CH_2)_2-$ | H | H | oil |
| 21 | " | 3 | $-(CH_2)_2-CO-(CH_2)_2-$ | 4-$CH_3$ | H | oil |
| 22 | " | 4 | $-(CH_2)_4-CO-(CH_2)_2-$ | H | H | 102–105 |
| 23 | $-N(CH_3)(OCH_3)$ | 4 | $-(CH_2)_4-CO-(CH_2)_2-$ | H | H | oil |
| 24 | " | 4 | $-(CH_2)_2-CO-(CH_2)_2-$ | 4-$CH_3$ | H | oil |
| 25 | " | 4 | $-(CH_2)_4-CO-(CH_2)_2-$ | H | H | oil |
| 26 | " | 3 | $-(CH_2)_2-CO-(CH_2)_2-$ | H | H | oil |
| 27 | " | 3 | $-(CH_2)_2-CO-(CH_2)_2-$ | 4-$CH_3$ | H | oil |
| 28 | " | 4 | $-CH(OH)-(CH_2)_2-$ | 4-$CH_3$ | H | oil |
| 29 | " | 4 | $-CH(OH)-(CH(CH_3)-CH_2-$ | 4-Cl | H | 106–111 |
| 30 | " | 4 | $-(CH_2)_2-CH(OH)-(CH_2)_2-$ | H | H | oil |
| 31 | " | 3 | $-(CH_2)_4-CH(OH)-$ | H | H | oil |
| 32 | $C_2H_5$ | 3 | $-CH(OH)-(CH_2)_2-$ | H | H | oil |
| 33 | " | 3 | $-CH(OH)-(CH_2)_2-$ | 4-$CH_3$ | H | |
| 34 | " | 3 | $-CH(OH)-(CH_2)_2-$ | 4-F | H | oil |
| 35 | $OCH_3$ | 3 | $-CO-(CH_2)_2-$ | 4-Cl | H | |
| 36 | $OC_2H_5$ | 3 | $-CO-(CH_2)_2-$ | 4-Cl | H | |
| 37 | $SCH_3$ | 3 | $-CO-(CH_2)_2-$ | 4-Cl | H | 123–125 |
| 38 | Cyclopropyl | 3 | $-CO-(CH_2)_2-$ | 4-Cl | H | |
| 39 | $C_2H_5$ | 3 | $-CO-(CH_2)_2-$ | 4-Cl | H | 83–85 |
| 40 | Cyclopropyl-amino | 3 | $-CO-(CH_2)_2-$ | 4-Cl | H | |
| 41 | 2,5-dimethylpyrrolidinyl | 3 | $-CO-(CH_2)_2-$ | 4-Cl | H | |
| 42 | $-NHCH_3$ | 3 | $-CO-(CH_2)_2-$ | 4-Cl | H | |
| 43 | $OCH_3$ | 4 | $-CH(OH)-(CH_2)_2-$ | 4-$CH_3$ | H | |

-continued

| No. | R¹ | Position of A | A | (4-position substituent) | (other substituent) | M.p. [°C.] |
|---|---|---|---|---|---|---|
| 44 | SCH₃ | 4 | —CH(OH)—(CH₂)₂— | 4-CH₃ | H | |
| 45 | C₂H₅ | 3 | —CO—(CH₂)₂— | 4-Cl | 4-Cl | |
| 46 | C₂H₅ | 3 | —CO—(CH₂)₂— | 4-Cl | 4-Br | |
| 47 | —N(CH₃)(OCH₃) | 4 | —CO—(CH₂)₃— | 4-CH₃ | 3-Cl | |
| 48 | " | 4 | —CO—(CH₂)₃— | 4-CH₃ | 3-CH₃ | |
| 49 | " | 4 | —CO—(CH₂)₃— | 4-CH₃ | 3-OCH₃ | |
| 50 | " | 4 | —CO—(CH₂)₃— | 4-CH₃ | 3-CF₃ | |
| 51 | Morpholin-4-yl | 3 | —CO—(CH₂)₂— | 4-Cl | H | |
| 52 | —N(CH₃)(OCH₃) | 4 | —CO—(CH₂)₂— | 3-Cl | H | |
| 53 | " | 4 | —CO—(CH₂)₂— | 4-CF₃ | H | |
| 54 | OCH₃ | 3 | —CO—(CH₂)₂— | H | H | 104–106 |
| 55 | OCH₃ | 3 | —CH(OH)—(CH₂)₂— | H | H | 76–78 |
| 56 | OCH₃ | 3 | —(CH₂)₂—CO— | H | H | 115–117 |
| 57 | —N(CH₃)(OCH₃) | 4 | —CH(OH)—(CH₂)₂— | H | 4-CF₃ | |
| 58 | " | 3 | —CO—(CH₂)₂— | H | 4-Br | |
| 59 | " | 3 | —CO—(CH₂)₂— | 2-CH₃ | H | 84–86 |
| 60 | " | 3 | —CO—(CH₂)₂— | 3-CH₃ | H | |
| 61 | " | 4 | —(CH₂)₂—CO— | 3-OC₆H₅ | H | oil |
| 62 | " | 4 | —CO—(CH₂)₂— | 4-C₆H₅ | H | 122–123 |
| 63 | " | 4 | —CO—(CH₂)₂— | 4-O—n-C₆H₁₃ | H | |
| 64 | " | 3 | —CH₂—CO— | 4-CH₃ | H | |
| 65 | " | 3 | —CH₂—CH(OH)— | 4-CH₃ | H | |
| 66 | " | 4 | —CO—CH₂— | 4-CH₃ | H | |
| 67 | " | 4 | —CH(OH)—CH₂— | 4-CH₃ | H | |
| 68 | " | 4 | —CO—(CH₂)₃— | 4-CH₃ | H | |
| 69 | " | 4 | —CH(OH)—(CH₂)₃— | 4-CH₃ | H | |
| 70 | " | 4 | —CO—CH₂—CH(CH₃)— | 4-CH₃ | H | |
| 71 | " | 3 | —CH(CH₃)—CH₂—CO— | 4-CH₃ | H | |
| 72 | " | 4 | —C(CH₃)₂—CH₂—CO— | H | H | |
| 73 | " | 3 | —C(CH₃)₂—CH₂—CO— | H | H | |
| 74 | " | 4 | —CO—(CH₂)₅— | H | H | |
| 75 | " | 4 | —CO—(CH₂)₇— | H | H | |
| 76 | " | 4 | —CO—(CH₂)₈— | H | H | |
| 77 | N(CH₃)₂ | 3 | —(CH₂)₂—CO— | H | H | 88–90 |
| 78 | —N(OCH₃)(CH₃) | 4 | —(CH₂)₂—CO— | 3-CF₃ | H | 108–109 |
| 79 | " | 4 | —CH₂—CH(CH₃)—(CH₂)₂—CO— | H | H | 65–67 |
| 80 | " | 4 | —(CH₂)₂—CO— | 3-Cl | H | 98–100 |
| 81 | —N(OC₂H₅)(CH₃) | 4 | —CO—(CH₂)₂— | 4-CH₃ | H | 71–72 |
| 82 | " | 4 | —CH(OH)(CH₂)₂— | 4-CH₃ | H | 63–64 |

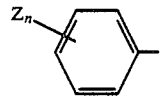

| No. | R¹ | Position of A | A | $Z_n$—phenyl | Y | M.p. [°C.] |
|---|---|---|---|---|---|---|
| 83 | C₂H₅ | 3 | —CO—(CH₂)₂— | β-naphthyl | H | |
| 84 | C₂H₅ | 3 | —CO—(CH₂)₂— | α-naphthyl | H | |
| 85 | —N(OCH₃)(CH₃) | 4 | —CO—(CH₂)₂— | β-naphthyl | H | 91–93 |

-continued

| No. | R¹ | Position of A | A | $Z_n$ | Y | M.p. [°C.] |
|---|---|---|---|---|---|---|
| 86 | " | 4 | —CO—(CH$_2$)$_2$— | α-naphthyl | H | 113–115 |
| 87 | " | 3 | —CO—(CH$_2$)$_2$— | β-naphthyl | H | |
| 88 | " | 3 | —CO—(CH$_2$)$_2$— | α-naphthyl | H | |
| 89 | " | 4 | —CO—(CH$_2$)$_2$— | 4-chloro-α-naphthyl | H | 61–63 |

| No. | R¹ | Position of A | A | $Z_n$ | Y | M.p. [°C.] |
|---|---|---|---|---|---|---|
| 90 | —N(OCH$_3$)(CH$_3$) | 4 | —(CH$_2$)$_2$—O— | 4-t-OC$_4$H$_9$ | H | 86–87 |
| 91 | " | 3 | —CO—(CH$_2$)$_2$— | 4-CH$_3$ | H | 90–92 |
| 92 | SCH$_3$ | 3 | —CO—(CH$_2$)$_2$— | 4-CH$_3$ | H | 145–147 |
| 93 | C$_2$H$_5$ | 3 | —CO—(CH$_2$)$_2$— | 4-CH$_3$ | H | 86–88 |
| 94 | —N(OCH$_3$)(CH$_3$) | 3 | —CH(OH)—(CH$_2$)$_2$—CH(CH$_3$)—CH$_2$— | H | H | oil |
| 95 | C$_2$H$_5$ | 3 | —CH$_2$—CO— | 4-CF$_3$ | H | 124–126 |
| 96 | —N(OCH$_3$)(CH$_3$) | 3 | —CO—(CH$_2$)$_2$— | 4-CH$_3$ | H | 112–113 |
| 97 | " | 3 | —CO—(CH$_2$)$_2$— | 4-CH$_3$ | H | 90–92 |
| 98 | " | 4 | —(CH$_2$)$_2$—CH(OH)— | 4-CH$_3$ | H | 107–108 |
| 99 | " | 4 | —CH(OH)—CH(CH$_3$)—CH$_2$— | H | H | oil |
| 100 | " | 3 | —CO—(CH$_2$)$_2$— | 2,4,6-(CH$_3$)$_3$ | H | oil |
| 101 | C$_2$H$_5$ | 3 | —CO—(CH$_2$)$_2$— | 2,4,6-(CH$_3$)$_3$ | H | 80–81 |
| 102 | OCH$_3$ | 3 | —CO—(CH$_2$)$_2$— | 2,4,6-(CH$_3$)$_3$ | H | 57–58 |
| 103 | SCH$_3$ | 3 | —CO—(CH$_2$)$_2$— | 2,4,6-(CH$_3$)$_3$ | H | 110–112 |
| 104 | N(CH$_3$)$_2$ | 3 | —CO—(CH$_2$)$_2$— | 2,4,6-(CH$_3$)$_3$ | H | 151–153 |
| 105 | —N(OCH$_3$)(CH$_3$) | 4 | —CO—(CH$_2$)$_2$— | 4-F | H | 94–96 |

The compounds of the formula I, and their acid addition salts, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrite, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 11 is intimately mixed with 97 parts by weight of particulate kaolin. A dust is obtained containing 3% by weight of the active ingredient.

VII. 30 parts by weight of compound no. 13 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 17 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. Preferably, the novel active ingredients are applied after emergence of the unwanted plants, both on cropland and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved and the growth stage of the plants, and varies from 0.05 to 10 kg/ha and more, but is preferably from 0.1 to 5 kg/ha. The higher application rates are particularly suitable for total elimination of vegetation.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate in this method was equivalent to 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. In the case of soybeans used for the postemergence treatment, peat was added to the substrate to ensure better growth. For this treatment, either plants which had been sown directly in the pots and grown there were selected, or plants which had been grown separately as seedlings and transplanted to the experiment vessels a few days before treatment. The application rates for postemergence treatment varied from ingredient to ingredient, and were either 0.25 or 0.5 kg of active ingredient per hectare. No covers were placed on the vessels in this treatment.

The pots were set up in the greenhouse—species from warmer areas at from 20° to 35° C. and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants employed in the experiments were *Amaranthus retroflexus, Avena sativa, Abutilon theophrasti, Arachys hypogaea, Chenopodium album, Cassia tora, Gossypium hirsutum, Glycine max., Euphorbia* geniculata, Lamium purpureum, Sida spinosa, Sinapis alba, Solanum nigrum, Triticum aestivum, and Zea mays.

On postemergence application, for example compounds nos. 1. 3, 5, 7, 11, 13, 17, and 79 had a good herbicidal action, particularly on broadleaved unwanted plants, and were at the same time selective in crop plants.

When applied preemergence, for example compound no. 1 had a herbicidal action in Sinapis alba, and compound no. 5 in oats.

In view of the good tolerance of the compounds according to the invention, and mixtures containing them, and the many application methods possible, they can be used in a further, large number of crops for removing unwanted plant growth.

The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape seed |
| Brassica napus var. napobrassica | |
| Brassica napus var. rapa | |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum | parsley |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva- crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis- idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds according to the invention, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

We claim:

1. An aniline derivative of the formula

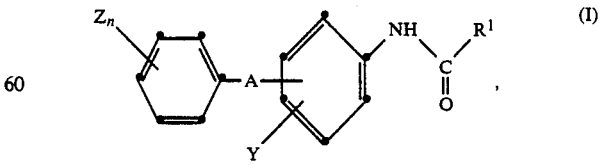

where $R^1$ is alkoxy, alkylthio or unsubstituted alkyl, halogen-substituted alkyl or $C_1$–$C_4$-alkoxy-substituted alkyl, each of which is of no more than 4 carbon atoms, or is cycloalkyl of 3 to 6 carbon atoms or the radical

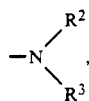

where $R^2$ and $R^3$ independently of one another are each hydrogen, alkyl or alkoxy, each of no more than 4 carbon atoms, or cycloalkyl of 3 to 6 carbon atoms, Y is hydrogen, halogen, methyl, methoxy or trifluoromethyl, A is an alkylene chain of 2 to 9 carbon atoms which contains a carbonyl group or a carbinol group of the formula

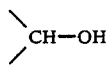

and can be substituted by methyl, Z is hydrogen, halogen, alkyl, alkoxy, haloalkyl or haloalkoxy, each of no more than 6 carbon atoms, or phenyl or phenoxy, and n is 1, 2 or 3, and the radical

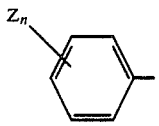

can be replaced by naphthyl which is unsubstituted or substituted by halogen, or by alkyl or alkoxy, each of no more than 4 carbon atoms.

2. An aniline derivative of the formula I as claimed in claim 1, where $R^1$ is

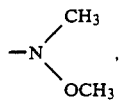

Y is hydrogen or halogen, A is —CO(CH$_2$)$_2$— para to the —NH—CO—$R^1$ group, Z is halogen or alkyl of no more than 4 carbon atoms, and n is 1.

3. An aniline derivative of the formula I as claimed in claim 1, where $R^1$ is

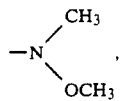

Y is hydrogen or chlorine, A is —CO—(CH$_2$)$_2$— para to the —NH—CO—$R^1$ group, Z is chlorine or methyl, and n is 1.

4. N-[4-(3-(2',4',6'-trimethylphenyl)-n-propan-3-onyl)-phenyl]-N'-methoxy-N'-methylurea.

5. A herbicide containing inert additives and from 0.1 to 95% by weight of an aniline derivative of the formula I as claimed in claim 1.

6. A process for combating the growth of unwanted plants, wherein a herbicidally effective amount of an aniline derivative of the formula I as claimed in claim 1 is allowed to act on the plants and/or their location.

7. An amine of the formula

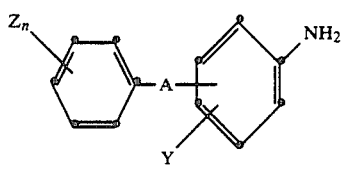 (II)

where A is an alkylene chain of from 2 to 9 carbon atoms which contains a carbonyl or carbinol group of the formula

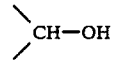

and which is unsubstituted or methyl-substituted, Y is hydrogen, halogen, methyl, methoxy or trifluoromethyl, Z is hydrogen, halogen, alkyl, alkoxy, haloalkyl or haloalkoxy, each of no more than 6 carbon atoms, phenyl or phenoxy, and n is 1, 2 or 3, and the radical

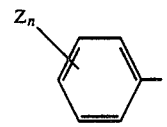

can be replaced by naphthyl which is unsubstituted or substituted by halogen, or by alkyl or alkoxy, each of no more than 4 carbon atoms.

8. A herbicide containing inert additives and from 0.5 to 90% by weight of an aniline derivative of the formula I as claimed in claim 1.

* * * * *